(12) United States Patent
Michihata

(10) Patent No.: US 12,075,970 B2
(45) Date of Patent: Sep. 3, 2024

(54) MEDICAL CONTROL DEVICE AND MEDICAL OBSERVATION SYSTEM

(71) Applicant: Sony Olympus Medical Solutions Inc., Tokyo (JP)

(72) Inventor: Taihei Michihata, Kanagawa (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 0 days.

(21) Appl. No.: 18/163,280

(22) Filed: Feb. 2, 2023

(65) Prior Publication Data

US 2023/0180997 A1    Jun. 15, 2023

Related U.S. Application Data

(63) Continuation of application No. 16/713,060, filed on Dec. 13, 2019, now abandoned.

(30) Foreign Application Priority Data

Mar. 1, 2019    (JP) .................................. 2019-037903

(51) Int. Cl.
*A61B 1/00*    (2006.01)
*A61B 1/04*    (2006.01)
(Continued)

(52) U.S. Cl.
CPC ...... *A61B 1/00006* (2013.01); *A61B 1/00009* (2013.01); *A61B 1/043* (2013.01);
(Continued)

(58) Field of Classification Search
CPC .......... A61B 1/00009; A61B 1/000094; A61B 1/005; A61B 1/00186; A61B 1/043;
(Continued)

(56) References Cited

U.S. PATENT DOCUMENTS 4,831,437 A * 5/1989 Nishioka ................ A61B 1/042
348/649
4,868,645 A * 9/1989 Kobayashi ............. A61B 1/042
348/69

(Continued)

FOREIGN PATENT DOCUMENTS

JP     2015047402 A * 3/2015
JP     2017000192 A * 1/2017

*Primary Examiner* — John P Leubecker
*Assistant Examiner* — Jae Woo
(74) *Attorney, Agent, or Firm* — XSENSUS LLP

(57) ABSTRACT

A medical control device includes: an imaging controller configured to control an imaging device to cause the imaging device to capture normal light emitted from a light source and received by way of an observation target in a first period to generate a first captured image, and to capture excitation light emitted from the light source and received by way of the observation target and fluorescence light from the observation target excited by the excitation light in a second period to generate a second captured image; and image processing circuitry configured to: perform an adjustment process to reduce a component of a color corresponding to the excitation light included in the second captured image; and generate a superimposed image by superimposing the first captured image and the second captured image subjected to the adjustment process.

17 Claims, 8 Drawing Sheets

(51) Int. Cl.
  *A61B 1/045* (2006.01)
  *A61B 1/05* (2006.01)
  *A61B 1/06* (2006.01)
  *G06T 7/00* (2017.01)
(52) U.S. Cl.
  CPC ............... *A61B 1/045* (2013.01); *A61B 1/05* (2013.01); *A61B 1/0638* (2013.01); *A61B 1/0655* (2022.02); *A61B 1/0661* (2013.01); *G06T 7/0012* (2013.01); *G06T 2207/10016* (2013.01); *G06T 2207/10024* (2013.01); *G06T 2207/10068* (2013.01)
(58) Field of Classification Search
  CPC ......... A61B 1/045; A61B 1/05; A61B 1/0638; G06T 2207/10016; G06T 2207/10024; G06T 2207/10068
  See application file for complete search history.

(56) References Cited

U.S. PATENT DOCUMENTS

| | | | | |
|---|---|---|---|---|
| 5,647,368 A | * | 7/1997 | Zeng | A61B 5/4255 600/476 |
| 6,473,637 B1 | * | 10/2002 | Hayashi | A61B 5/0071 600/477 |
| 2002/0013512 A1 | * | 1/2002 | Sendai | A61B 5/0084 600/118 |
| 2002/0175993 A1 | * | 11/2002 | Ueno | A61B 5/0071 348/68 |
| 2005/0261592 A1 | * | 11/2005 | Suga | A61B 1/0655 600/478 |
| 2006/0058684 A1 | * | 3/2006 | Sendai | A61B 1/00186 600/476 |
| 2006/0247535 A1 | * | 11/2006 | Sendai | A61B 1/0638 600/476 |
| 2006/0256191 A1 | * | 11/2006 | Iketani | A61B 1/0005 348/65 |
| 2008/0239070 A1 | * | 10/2008 | Westwick | A61B 1/043 348/E5.029 |
| 2013/0286175 A1 | * | 10/2013 | Hashimoto | H04N 23/56 348/68 |
| 2016/0041098 A1 | * | 2/2016 | Hirawake | A61B 1/0655 250/206 |
| 2018/0000401 A1 | * | 1/2018 | Kang | A61B 1/063 |
| 2019/0216325 A1 | * | 7/2019 | Ouyang | A61B 1/00096 |
| 2020/0364862 A1 | | 11/2020 | DaCosta et al. | |
| 2023/0000329 A1 | * | 1/2023 | Kono | H04N 23/555 |

* cited by examiner

MEDICAL CONTROL DEVICE AND MEDICAL OBSERVATION SYSTEM

CROSS-REFERENCE TO RELATED APPLICATIONS

This application is a continuation of U.S. application Ser. No. 16/713,060, filed Dec. 13, 2019, which claims priority from Japanese Application No. 2019-037903, filed on Mar. 1, 2019, the contents of each are incorporated by reference herein in its entirety.

BACKGROUND

The present disclosure relates to a medical control device and a medical observation system.

In the related art, there is known a photo dynamic diagnosis device which performs a photo dynamic diagnosis (PDD) which is one of cancer diagnosis methods to detect a cancer cell (for example, see JP 2016-202726 A).

In the photo dynamic diagnosis, for example, a photosensitizer such as 5-aminolaevulinic acid (hereinbelow, referred to as 5-ALA) is used. The 5-ALA is a natural amino acid originally contained in organisms of animals and plants. The 5-ALA is taken into a cell after being injected into a body, and biosynthesized to protoporphyrin in mitochondria. Then, the protoporphyrin is excessively accumulated in a cancer cell. In addition, the protoporphyrin excessively accumulated in the cancer cell has photoactivity. Therefore, the protoporphyrin emits fluorescence (for example, red fluorescence in a wavelength band of 600 to 740 nm) when excited by excitation light (for example, blue visible light in a wavelength band of 375 to 445 nm). In this way, the cancer diagnosis method for causing cancer cells to fluorescently emit using a photosensitizer is called photo dynamic diagnosis.

Then, the photo dynamic diagnosis device disclosed in JP 2016-202726 A includes a fluorescence imaging device which captures fluorescence from the photosensitizer excited by the excitation light to generate fluorescence captured image, and an optical filter which is provided in the front stage of the optical path of the fluorescence imaging device and cuts all the excitation light facing the fluorescence imaging device.

SUMMARY

By the way, in a case where all the excitation light facing the fluorescence imaging device is cut by the optical filter, the fluorescence imaging device captures only the fluorescence from the photosensitizer. In this way, in a case where only the fluorescence is captured, the fluorescence captured image is an image containing only a fluorescent component (cancer cell), and becomes an image of which the background (a tissue around the fluorescence portion) is not visible. Therefore, a physician is not able to view the background even though the physician observes the fluorescence captured image. Thus, it is hard to recognize a position of the cancer cell. The photo dynamic diagnosis device disclosed in JP 2016-202726 A includes an illumination light imaging device separately from the fluorescence imaging device, which captures illumination light (visible light) reflected on an observation target to generate an illumination light captured image. In other words, the background becomes visible by observing the illumination light captured image. However, there is needed to prepare two imaging devices, and a simplification of structure is not achievable.

Herein, as a configuration using only one fluorescence imaging device, it is considered that the background becomes visible in the fluorescence captured image by the excitation light component by passing part of the excitation light without cutting all the excitation light facing the fluorescence imaging device by the optical filter. However, a balance in brightness between a fluorescent component and the excitation light component in the fluorescence captured image does not become a desired balance due to manufacture variations of the optical filter, temperature change, and an aging degradation, and the fluorescence captured image may not form an image suitable for observation.

There is a need for a medical control device and a medical observation system which may generate an image suitable for observation while achieving a simple structure.

According to one aspect of the present disclosure, there is provided a medical control device including: an imaging controller configured to control an imaging device to cause the imaging device to capture normal light emitted from a light source and received by way of an observation target in a first period to generate a first captured image, and to capture excitation light emitted from the light source and received by way of the observation target and fluorescence light from the observation target excited by the excitation light in a second period to generate a second captured image; and image processing circuitry configured to: perform an adjustment process to reduce a component of a color corresponding to the excitation light included in the second captured image; and generate a superimposed image by superimposing the first captured image and the second captured image subjected to the adjustment process.

DETAILED DESCRIPTION

Figure 1:
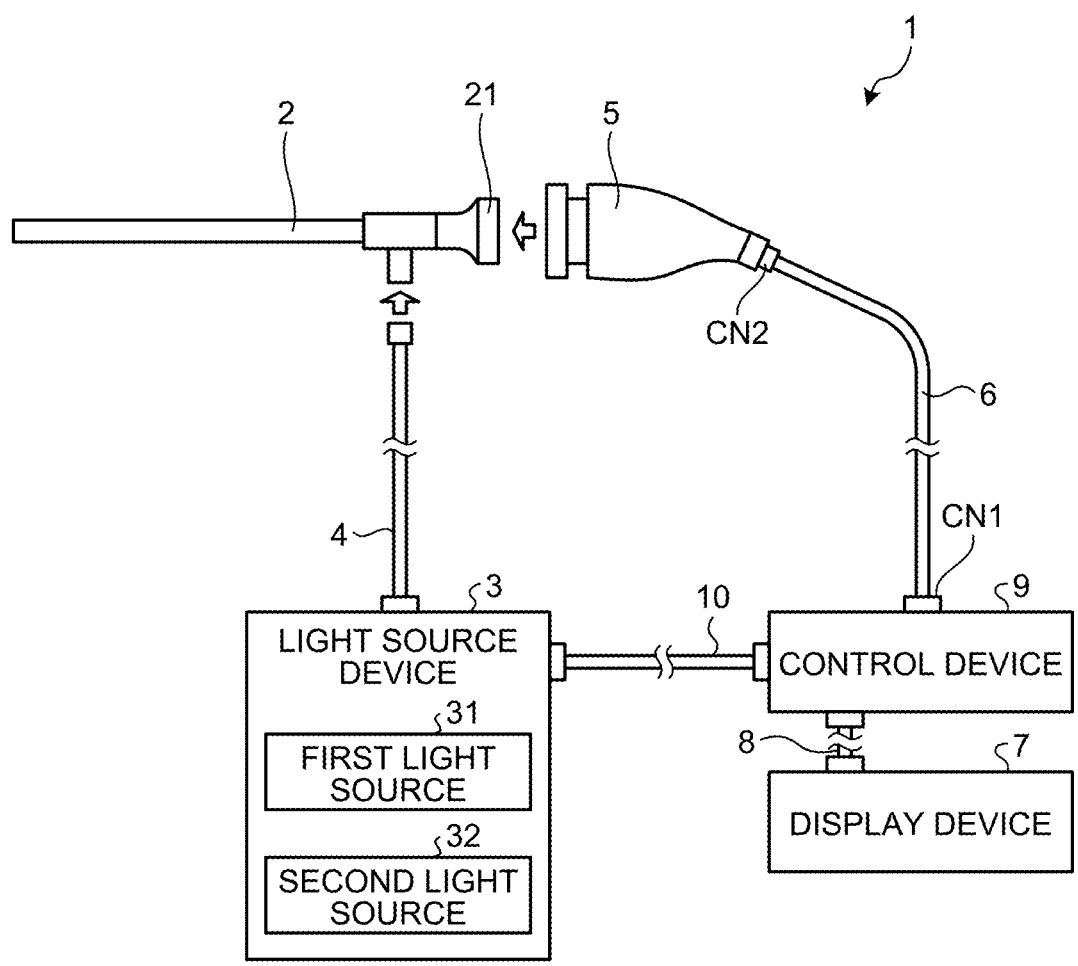
FIG. 1 is a diagram illustrating a configuration of a medical observation system according to a first embodiment.

Hereinbelow, modes (hereinafter, referred to as embodiments) for carrying out the disclosure will be described with reference to the drawings. Further, this disclosure is not limited to the following embodiments. Further, the same portions in the drawings will be attached with the same symbol.

First Embodiment

Schematic Configuration of Medical Observation System

FIG. 1 is a diagram illustrating a configuration of the medical observation system 1 according to a first embodiment.

The medical observation system 1 is a system which is used in medical fields to capture (observe) an image of an organism (observation target) which is a subject. The medical observation system 1 includes, as illustrated in FIG. 1, an insertion portion 2, a light source device 3, a light guide 4, a camera head 5, a first transfer cable 6, a display device 7, a second transfer cable 8, a control device 9, and a third transfer cable 10.

In the first embodiment, the insertion portion 2 is configured by a rigid endoscope. In other words, the insertion portion 2 is an elongated shape of which the entire portion is rigid, or some portion is soft and other parts are rigid, and is inserted into the organism. In the insertion portion 2, one or a plurality of lenses are provided, and an optical system is provided to condense light from the subject.

The light source device 3 is connected to one end of the light guide 4, and supplies the one end of the light guide 4 with light with which the organism is irradiated under the control of the control device 9. The light source device 3 includes, as illustrated in FIG. 1, a first light source 31 and a second light source 32.

The first light source 31 outputs (emits) normal light of a first wavelength band. In the first embodiment, the first light source 31 is configured by a Light Emitting Diode (LED) which emits white light.

The second light source 32 outputs (emits) excitation light of a second wavelength band different from the first wavelength band. In the first embodiment, the second light source 32 is configured by a semiconductor laser which emits excitation light of a blue wavelength band (for example, a wavelength band of 375 nm to 445 nm) at which protoporphyrin is excited. In addition, the protoporphyrin emits fluorescence of a red wavelength band (for example, a wavelength band of 600 nm to 740 nm) when excited by the excitation light.

Further, in the first embodiment, the description is given about a case where the excitation light is used as the light of a blue wavelength band, and the fluorescence is used as the light of a red wavelength band, but the disclosure is not limited thereto. For example, other configurations may be employed as long as the excitation light is light of wavelength band of one of two wavelength bands of red, green and blue, and the fluorescence is light of the other one of the two wavelength bands.

Then, in the light source device 3, the first light source 31 is driven in a first period in the repeated first and second periods under the control of the control device 9. In other words, in the first period, the light source device 3 emits the normal light (white light). In addition, in the light source device 3, the second light source 32 is driven in the second period under the control of the control device 9. In other words, in the second period, the light source device 3 emits the excitation light.

Further, in the first embodiment, the light source device 3 is configured separately from the control device 9. However, the disclosure is not limited to the above configuration, but the light source device may be provided in the control device 9.

The one end of the light guide 4 is detachably connected to the light source device 3, and the other end is detachably connected to the insertion portion 2. Then, the light guide 4 transfers the light (the normal light or the excitation light) supplied from the light source device 3 from one end to the other end, and supplies the light to the insertion portion 2. The light supplied to the insertion portion 2 is output from the distal end of the insertion portion 2, and the organism is irradiated with the light. In a case where the organism is irradiated with the normal light (white light), the normal light (the normal light reflected on the organism) received by way of the organism is condensed by an optical system in the insertion portion 2. Further, in the following, for the convenience of explanation, the normal light condensed by the optical system in the insertion portion 2 is referred to as a first subject image. In addition, in a case where the organism is irradiated with the excitation light, the excitation light (the excitation light reflected on the organism) received by way of the organism and the fluorescence which is emitted from the excited protoporphyrin condensed in a lesion portion in the organism are condensed by the optical system in the insertion portion 2. Further, in the following, for the convenience of explanation, the excitation light and the fluorescence condensed by the optical system in the insertion portion 2 will be referred to as a second subject image.

The camera head 5 corresponds to an imaging device according to this disclosure. The camera head 5 is detachably connected to the proximal end (an eyepiece portion 21 (FIG. 1)) of the insertion portion 2. Then, the camera head 5 captures the first subject image (normal light) and the second subject image (the excitation light and the fluorescence) condensed by the insertion portion 2 under the control of the control device 9, and outputs an image signal (RAW signal) of the capturing. The image signal is, for example, an image signal of 4 K or more.

Further, the detailed configuration of the camera head 5 will be described below.

The first transfer cable 6 is configured such that one end thereof is detachably connected to the control device 9 through a connector CN1 (FIG. 1), and the other end is detachably connected to the camera head 5 through a connector CN2 (FIG. 1). Then, the first transfer cable 6 transfers the image signal output from the camera head 5 to the control device 9, and transfers a control signal, a synchronization signal, a clock, and power output from the control device 9 to the camera head 5.

Further, the image signal from the camera head 5 to the control device 9 through the first transfer cable 6 may be transferred by an optical signal, or may be transferred by an electrical signal. The control signal, the synchronization signal, and the clock may be similarly transferred from the control device 9 to the camera head 5 through the first transfer cable 6.

The display device 7 is configured by a display device using a liquid crystal, organic Electro Luminescence (EL), or the like, and displays an image based on a video signal from the control device 9 under the control of the control device 9.

One end of the second transfer cable 8 is detachably connected to the display device 7, and the other end is detachably connected to the control device 9. The second transfer cable 8 transfers a video signal processed in the control device 9 to the display device 7.

The control device 9 corresponds to the medical control device according to this disclosure. The control device 9 is configured by a Central Processing Unit (CPU) and a Field-Programmable Gate Array (FPGA), and collectively controls the operations of the light source device 3, the camera head 5, and the display device 7.

Further, the detailed configuration of the control device 9 will be described below.

One end of the third transfer cable 10 is detachably connected to the light source device 3, and the other end is detachably connected to the control device 9. Then, the third transfer cable 10 transfers the control signal from the control device 9 to the light source device 3.

Configuration of Camera Head

Next, the configuration of the camera head 5 will be described.

Figure 2:
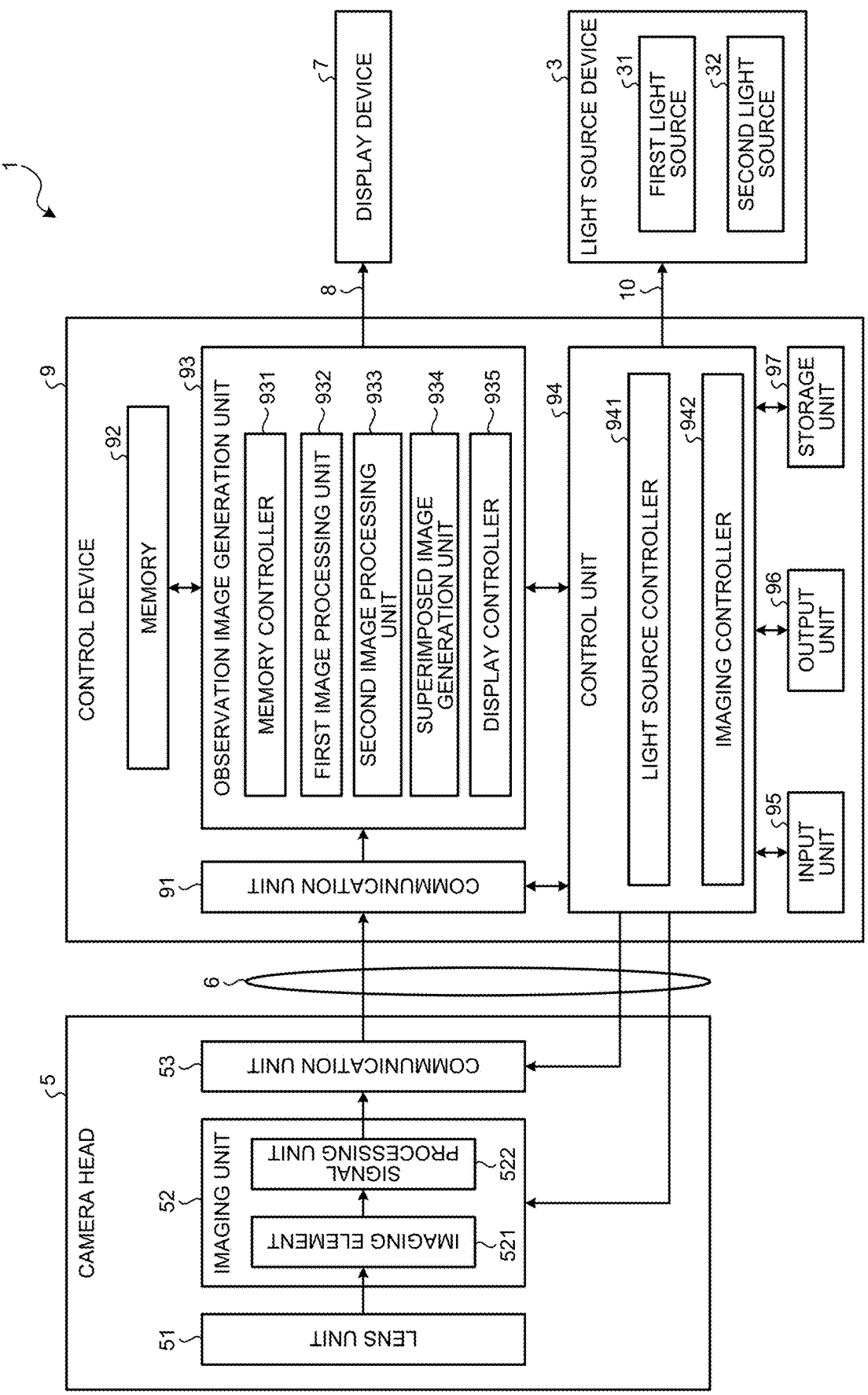
FIG. 2 is a block diagram illustrating a configuration of a camera head and a control device.

FIG. 2 is a block diagram illustrating a configuration of the camera head 5 and the control device 9.

Further, in FIG. 2, for the convenience of explanation, the connectors CN1 and CN2 between the control device 9 and the camera head 5 and the first transfer cable 6, the connectors between the control device 9 and the display device 7 and the second transfer cable 8, and the connectors between the control device 9 and the light source device 3 and the third transfer cable 10 are omitted.

The camera head 5 includes a lens unit 51, an imaging unit 52, and a communication unit 53 as illustrated in FIG. 2.

The lens unit 51 is configured using one or a plurality of lenses, and forms the first subject image (normal light) and the second subject image (the excitation light and the fluorescence) condensed by the insertion portion 2 in an imaging plane of the imaging unit 52 (an imaging element 521).

The imaging unit 52 captures an image of the organism under the control of the control device 9. The imaging unit 52 includes the imaging element (imaging sensor) 521 and a signal processing unit 522 as illustrated in FIG. 2.

The imaging element 521 is configured by a CCD (Charge Coupled Device) or a CMOS (Complementary Metal Oxide Semiconductor) which receives the first subject image (normal light) and the second subject image (the excitation light and the fluorescence) formed by the lens unit 51, and converts the images into electrical signals (analog signals). Then, the imaging element 521 repeatedly captures an image in the first and second periods in an alternate manner in synchronization with light emitting timing of the light source device 3 under the control of the control device 9. In the following, for the convenience of explanation, an image generated by capturing the first subject image (normal light) in the first period by the imaging element 521 is referred to as a normal light image (corresponding to a first captured image according to this disclosure), and an image generated by capturing the second subject image (the excitation light and the fluorescence) in the second period by the imaging element 521 will be referred to as a PDD image (corresponding to a second captured image according to this disclosure). In addition, the normal light image and the PDD image will be collectively referred to as a captured image.

The signal processing unit 522 performs signal processing on the captured image (analog signal) generated by the imaging element 521 to output the captured image (the RAW signal (digital signal)).

The communication unit 53 serves as a transmitter which transmits the captured image (the RAW signal (digital signal)) output from the imaging unit 52 through the first transfer cable 6 to the control device 9. For example, the communication unit 53 is configured by a high speed serial interface which performs communication of the captured image at a transmission rate of 1 Gbps or more with respect to the control device 9 through the first transfer cable 6.

Configuration of Control Device

Next, the configuration of the control device 9 will be described with reference to FIG. 2.

The control device 9 includes a communication unit 91, a memory 92, an observation image generation unit 93, a control unit 94, an input unit 95, an output unit 96, and a storage unit 97 as illustrated in FIG. 2.

The communication unit 91 serves as a receiver which receives the captured image (the RAW signal (digital signal)) output from the camera head 5 (the communication unit 53) through the first transfer cable 6. For example, the communication unit 91 is configured by a high speed serial interface which performs communication of the captured image at a transmission rate of 1 Gbps or more with respect to the communication unit 53.

The memory 92 is configured by, for example, a Dynamic Random Access Memory (DRAM). The memory 92 may temporarily store a plurality of frames of the captured image sequentially output from the camera head 5 (the communication unit 53).

The observation image generation unit 93 processes the captured image (the RAW signal (digital signal)) which is output sequentially from the camera head 5 (the communication unit 53) and received by the communication unit 91 under the control of the control unit 94. The observation image generation unit 93 includes a memory controller 931, a first image processing unit 932, a second image processing unit 933, a superimposed image generation unit 934, and a display controller 935 as illustrated in FIG. 2.

The memory controller 931 controls writing and reading of the captured image with respect to the memory 92. More specifically, the memory controller 931 sequentially writes in the memory 92 the captured image (the normal light image and the PDD image) which is sequentially output from the camera head 5 (the communication unit 53) and received by the communication unit 91. In addition, when reading the normal light image from the memory 92 at a specific timing, the memory controller 931 inputs the read normal light image to the first image processing unit 932. Further, when reading the PDD image from the memory 92 at a specific timing, the memory controller 931 inputs the read PDD image to the second image processing unit 933.

The first image processing unit 932 corresponds to an image processing unit according to this disclosure. The first image processing unit 932 performs first image processing on the input normal light image (the RAW signal (digital signal)).

Examples of the first image processing include an optical black subtraction, a white balance adjustment, demosaic processing, color correction matrix processing, a gamma correction, and YC processing in which an RGB signal (the normal light image) is converted into a luminance signal and a chrominance signal (Y, $C_B/C_R$ signal).

The second image processing unit 933 performs second image processing different from the first image processing on the input PDD image (the RAW signal (digital signal)).

As the second image processing, similarly to the first image processing, the optical black subtraction, the white balance adjustment, the demosaic processing, the color correction matrix processing, the gamma correction, and the YC processing in which an RGB signal (PDD image) is converted into a luminance signal and a chrominance signal (Y, $C_B/C_R$ signal) may be exemplified.

In addition, the second image processing includes an adjustment process and a color changing process described below.

The adjustment process is a process of eliminating or reducing components (including the excitation light component) other than the fluorescence component included in the PDD image. Specifically, the excitation light is the light of a blue wavelength band. In addition, the fluorescence is the light of a red wavelength band. Therefore, in the adjustment process, the component (G value and the component (B value) of the excitation light) other than the component (R value) of the fluorescence is eliminated or reduced from among the R, G, B pixel values included in the PDD image (G and B values are set to "0" or predetermined values). For example, in the white balance adjustment, G and B values other than R value may be eliminated or reduced from the R, G, and B pixel values included in the PDD image by appropriately adjusting gains by which the R, G, and B pixel values are multiplied. In addition, for example, in the color correction matrix processing, G and B values other than R value may be eliminated or reduced from the R, G, and B pixel values included in the PDD image by appropriately adjusting a color correction matrix by which an input matrix which has the R, G, and B pixel values included in the PDD image as matrix elements is multiplied.

The color changing process is a process in which a pixel position (a pixel position where protoporphyrin is excited) where a luminance value becomes a specific threshold or more in the entire image region of the PDD image is converted into a specific color (for example, a color different from the fluorescence (red)).

In other words, the second image processing unit 933 corresponds to an adjustment processing unit according to this disclosure.

The superimposed image generation unit 934 performs a superimposing process in which the PDD image subjected to the second image processing by the second image processing unit 933 is superimposed with the normal light image subjected to the first image processing by the first image processing unit 932 so as to generate a superimposed image.

Herein, as the superimposing process, a first superimposing process and a second superimposing process below may be exemplified. Further, in the following, a region configured by a pixel of which the luminance value is equal to or more than a specific threshold in the PDD image will be referred to as a fluorescent region.

The first superimposing process is a process of replacing a region which is at the same pixel position as the fluorescent region in the normal light image with an image of the fluorescent region in the PDD image.

The second superimposing process is a process of changing a brightness of the color showing the fluorescence assigned to each pixel of the region which is at the same pixel position as the fluorescent region in the normal light image according to the luminance value of each pixel position in the fluorescent region of the PDD image.

The display controller 935 generates a video signal to display a superimposed image generated by the superimposed image generation unit 934 under the control of the control unit 94. Then, the display controller 935 outputs the video signal to the display device 7 through the second transfer cable 8.

The control unit 94 is configure by, for example, the CPU and the FPGA, and outputs the control signal through the first to third transfer cables 6, 8, and 10, so that the operations of the light source device 3, the camera head 5, and the display device 7 are controlled, and the entire operation of the control device 9 is controlled. The control unit 94 includes a light source controller 941 and an imaging controller 942 as illustrated in FIG. 2. Further, the functions of the light source controller 941 and the imaging controller 942 will be described in "Control Device" described below.

The input unit 95 is configured by an operation device such as a mouse, a keyboard, and a touch panel, and receives a user operation from a user such as a physician. Then, the input unit 95 outputs an operation signal corresponding to the user operation to the control unit 94.

The output unit 96 is configured by a speaker and a printer, and outputs various types of information.

The storage unit 97 stores a program executed by the control unit 94, and information necessary for the process of the control unit 94.

Operation of Control Device

Next, the operation of the control device 9 will be described.

Figure 3:
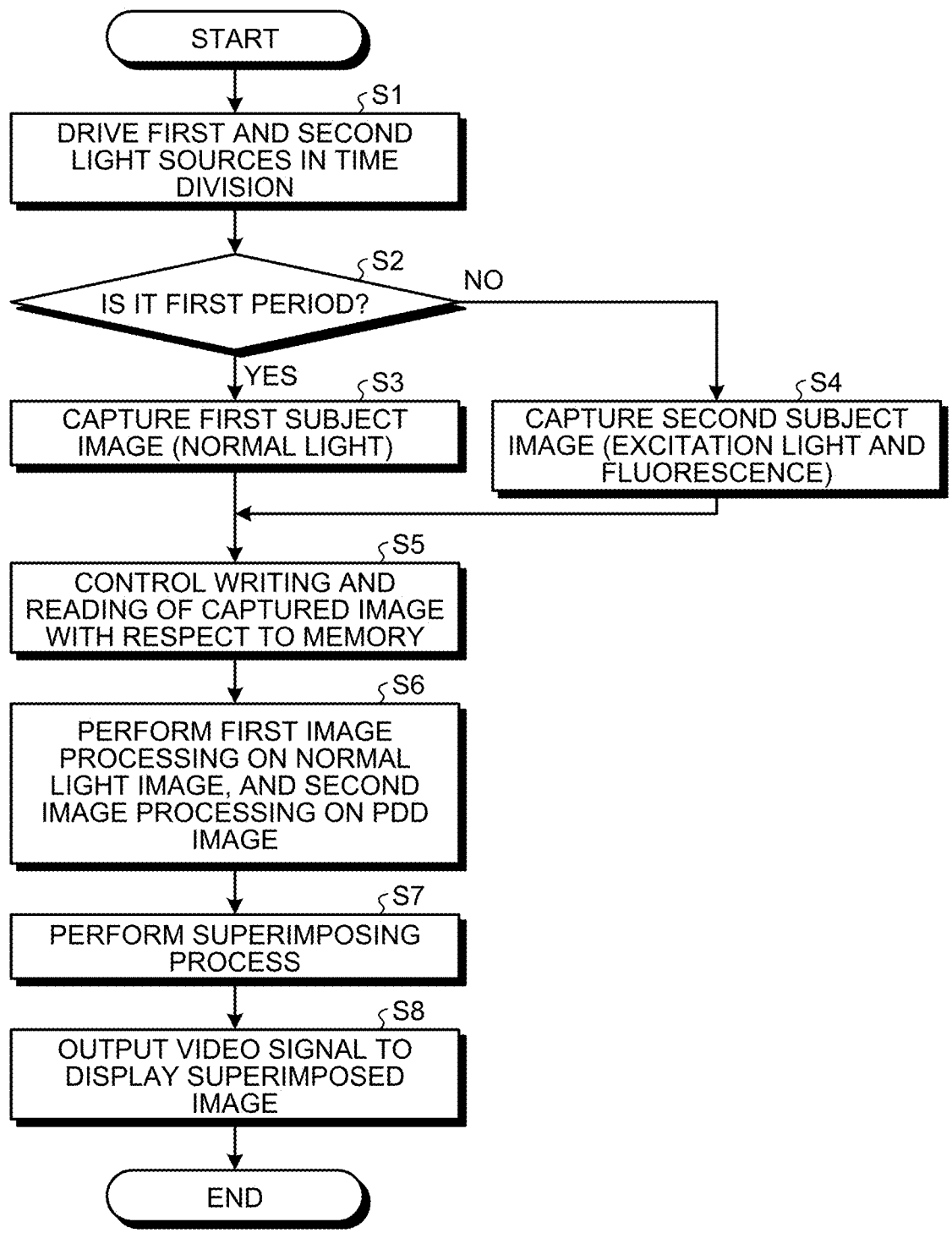
FIG. 3 is a flowchart illustrating an operation of the control device.
Figure 4:
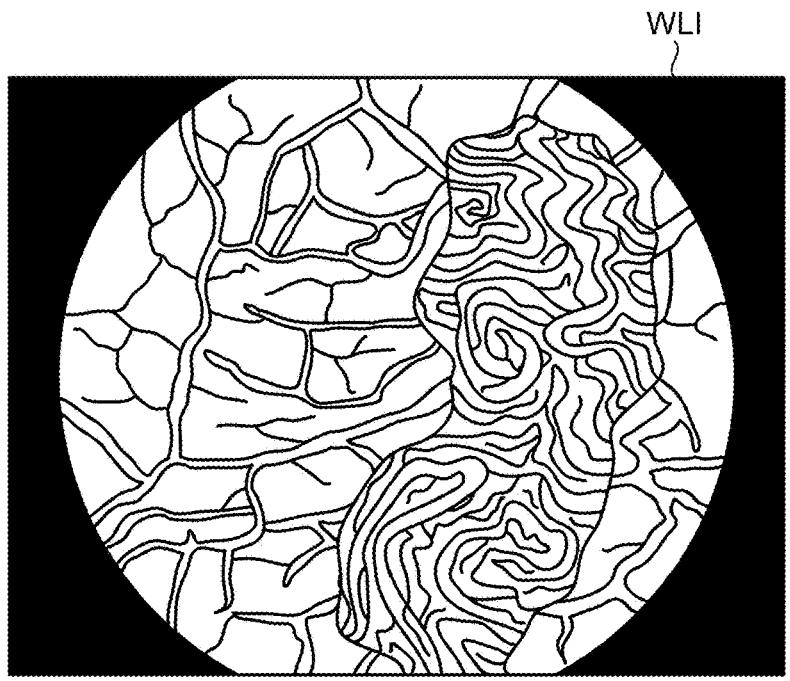
FIG. 4 is a diagram for describing an operation of the control device.
Figure 5:
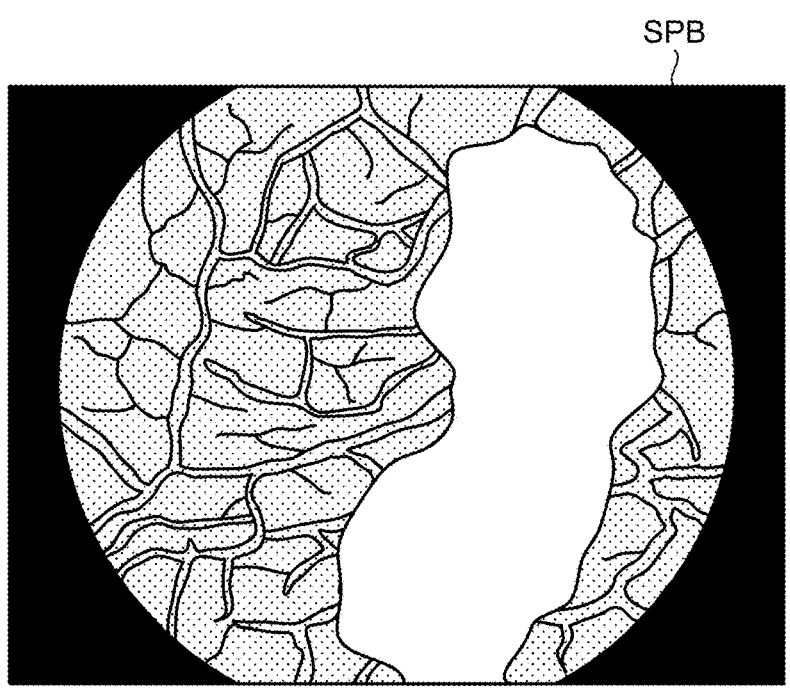
FIG. 5 is a diagram for describing an operation of the control device.
Figure 6:
FIG. 6 is a diagram for describing an operation of the control device.
Figure 7:
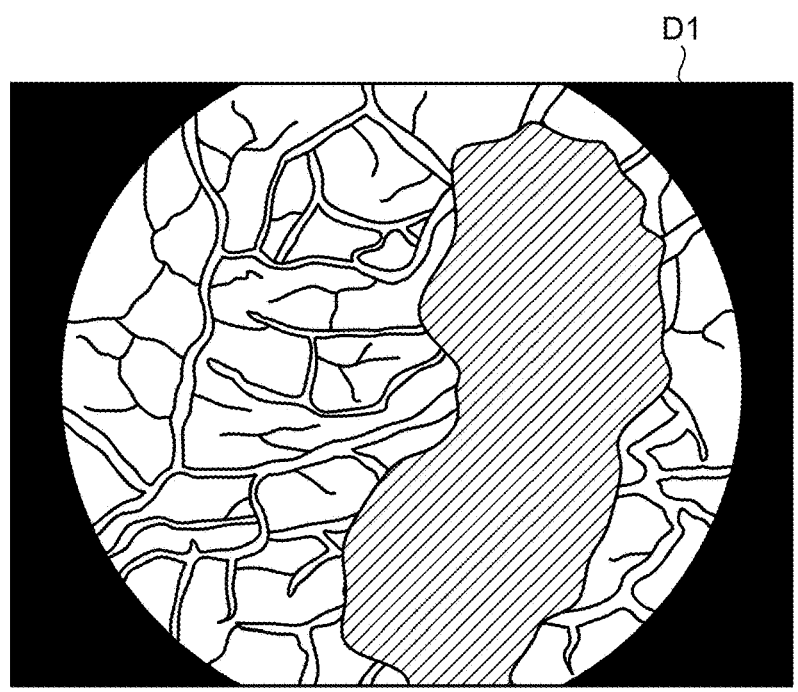
FIG. 7 is a diagram for describing an operation of the control device.

FIG. 3 is a flowchart illustrating the operation of the control device 9. FIGS. 4 to 7 are diagrams for describing the operation of the control device 9. Specifically, FIG. 4 is a diagram illustrating a normal light image WLI of one frame. FIG. 5 is a diagram illustrating a PDD image SPB of one frame which is read out of the memory 92 by the memory controller 931 and input to the second image processing unit 933. Further, in FIG. 5, a region (fluorescent region) of the fluorescent component fluorescently emitted from the protoporphyrin excited by the excitation light in the organism in the PDD image SPB is expressed with white, and the other regions (the regions of the excitation light component) other than the fluorescent region is expressed with dots. FIG. 6 is a diagram illustrating a PDD image SPA obtained by performing the second image processing on the PDD image SPB. FIG. 7 is a diagram illustrating a superimposed image D1 of one frame which is generated by the superimposed image generation unit 934.

First, the light source controller 941 performs a time-division driving of the first and second light sources 31 and 32 (Step S1). Specifically, in Step S1, in the repeating first and second periods in an alternate manner, the light source controller 941 causes the first light source 31 to emit light in the first period, and causes the second light source 32 to emit light in the second period on the basis of the synchronization signal.

After Step S1, the imaging controller 942 causes the imaging element 521 to capture the first and second subject images in the first and second periods in synchronization with light emitting timing of the first and second light sources 31 and 32 on the basis of the synchronization signal (Steps S2 to S4). In other words, the imaging element 521 captures the first subject image (normal light) to generate the normal light image in the case of the first period (Step S2: Yes), that is, a case where the organism is irradiated with the normal light (white light) (Step S3). On the other hand, the imaging element 521 captures the second subject image (the excitation light and the fluorescence) to generate the PDD image in the case of the second period (Step S2: No), that is, a case where the organism is irradiated with the excitation light (Step S4).

After Steps S3 and S4, the memory controller 931 controls writing and reading the captured image with respect to the memory 92 on the basis of the synchronization signal (Step S5).

After Step S5, the first and second image processing units 932 and 933 performs a process described below (Step S6).

In other words, the first image processing unit 932 sequentially performs the first image processing on the normal light image (for example, the normal light image WLI illustrated in FIG. 4) which is sequentially read out of the memory 92 by the memory controller 931.

In addition, the second image processing unit 933 sequentially performs the second image processing on each PDD image (for example, the PDD image SPB illustrated in FIG. 5) which is sequentially read out of the memory 92 by the memory controller 931. Herein, the second image processing includes the adjustment process. Therefore, for example, as illustrated in FIGS. 5 and 6, if the adjustment process is performed on the PDD image SPB, the PDD image SPA is generated in which the pixel value of the region (expressed with dots in FIG. 5) of the excitation light component other than the fluorescent region (expressed with white in FIG. 5) included in the PDD image SPB is set to "0" or a predetermined value (expressed with black in FIG. 6). In addition, the second image processing includes the color changing process. Therefore, for example, as illustrated in FIGS. 5 and 6, if the color changing process is performed on the PDD image SPB, the PDD image SPA is generated in which the fluorescent region (expressed with white in FIG. 5) included in the PDD image SPB is changed to a specific color (expressed with shadows in FIG. 6).

After Step S6, the superimposed image generation unit 934 performs the superimposing process in which each PDD image (for example, the PDD image SPA illustrated in FIG. 6) sequentially output from the second image processing unit 933 is superimposed with each normal light image (for example, the normal light image WLI illustrated in FIG. 4) sequentially output from the first image processing unit 932 to sequentially generate a superimposed image (for example, the superimposed image D1 illustrated in FIG. 7) (Step S7).

After Step S7, the display controller 935 sequentially generates a video signal to display each superimposed image (for example, the superimposed image D1 illustrated in FIG. 7) sequentially generated by the superimposed image generation unit 934, and sequentially outputs the video signal to the display device 7 (Step S8). With this configuration, the superimposed image (for example, the superimposed image D1 illustrated in FIG. 7) is sequentially displayed in the display device 7.

According to the first embodiment described above, the following effects are achieved.

The control device 9 according to the first embodiment causes the light source device 3 to emit the normal light in the first period, and causes the light source device 3 to emit the excitation light in the second period in the repeating first and second periods in an alternate manner. In addition, the control device 9 captures the first subject image (normal light) in the first period to generate the normal light image, and captures the second subject image (the excitation light and the fluorescence) in the second period to generate the PDD image. Then, the control device 9 performs the first image processing on the normal light image, and performs the second image processing including the adjustment process on the PDD image. In other words, the excitation light component included in the PDD image is eliminated or reduced by the adjustment process. Therefore, there is no need to use a known optical filter to cut the excitation light.

Then, a physician observes the normal light image (for example, the normal light image WLI illustrated in FIG. 4) (in the first embodiment, the superimposed image (for example, the superimposed image D1 illustrated in FIG. 7 is observed)) other than the PDD image (for example, the PDD image SPA illustrated in FIG. 6) after a second adjustment process is performed. Therefore, the physician may recognize a position of the organism where a cancer cell corresponding to the region of the fluorescence component exists. Therefore, the control device 9 may generate an image which is suitable to observation.

In addition, as the configuration of the medical observation system 1, a single plate type is employed in which only one imaging element 521 is provided, and the known optical filter is not used, so that it is possible to simplify the structure.

In particular, in the adjustment process, the component (G value and the component (B value) of the excitation light) other than the component (R value) of the fluorescence is eliminated or reduced from among the R, G, B pixel values included in the PDD image. In addition, the second image processing includes the color changing process.

Therefore, it is possible to strongly display the region (corresponding to a cancer cell) of the fluorescence component compared to the other regions. Therefore, the control device 9 may generate an image which is more suitable to observation.

Second Embodiment

Next, a second embodiment will be described.

In the following description, the same configurations as those of the first embodiment will be attached with the same symbol, and the detailed description will be omitted or simplified.

Figure 8:
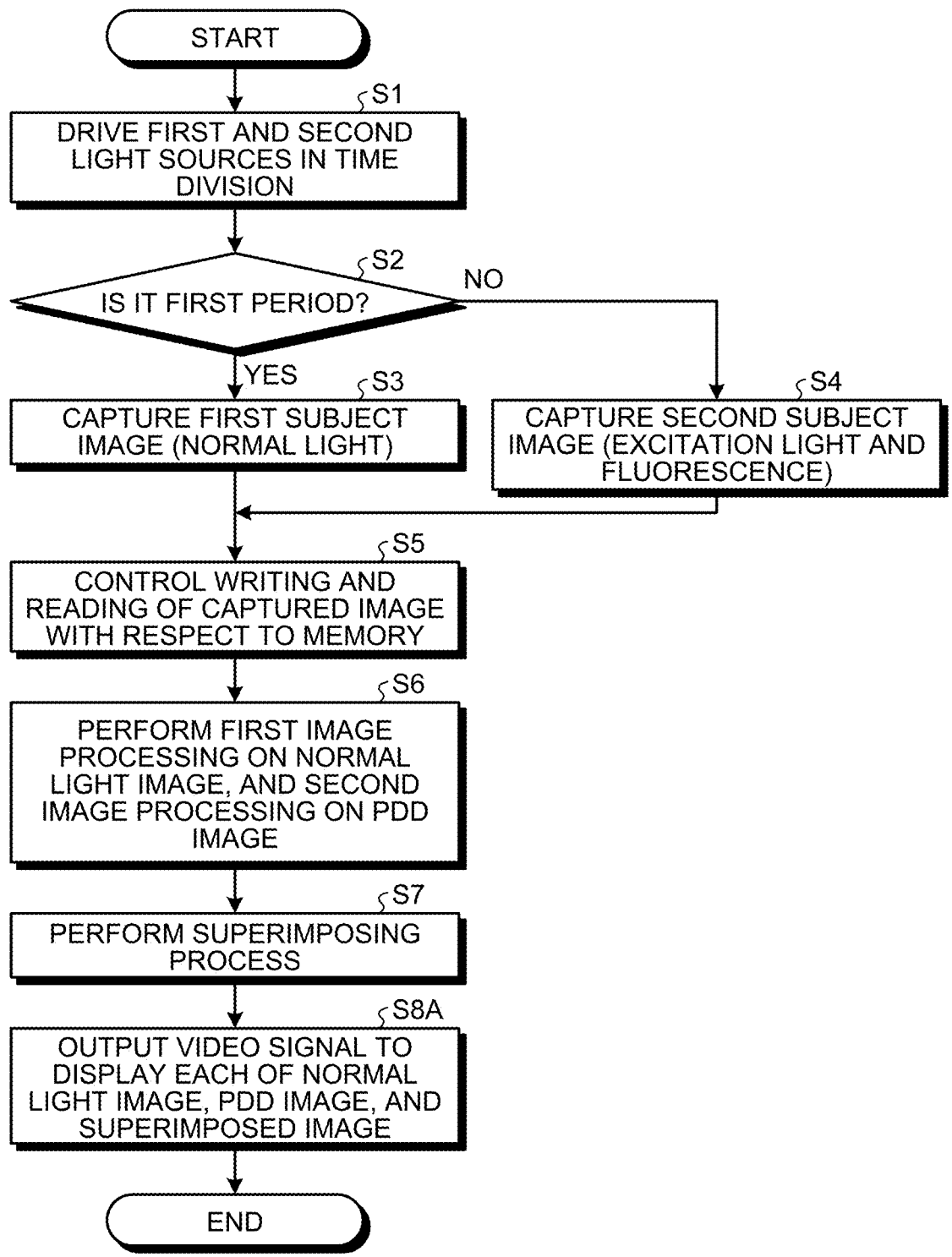
FIG. 8 is a flowchart illustrating an operation of the control device according to a second embodiment.

FIG. 8 is a flowchart illustrating an operation of the control device 9 according to a second embodiment.

In the second embodiment, only the image displayed in the display device 7 is different from the first embodiment. In other words, in the second embodiment, only the function of the display controller 935 is different from the first embodiment.

In the following, the function of the display controller 935 will be described with reference to FIG. 8.

The operation of the control device 9 according to the second embodiment is different in that Step S8A is employed instead of Step S8 as illustrated in FIG. 8.

Specifically, the display controller 935 performs a picture-in-picture process in Step S8A, sequentially generates a video signal to simultaneously display three images such as each normal light image (for example, the normal light image WLI illustrated in FIG. 4) sequentially output from the first image processing unit 932, each PDD image (for example, the PDD image SPA illustrated in FIG. 6) sequentially output from the second image processing unit 933, and each superimposed image which is sequentially generated by the superimposed image generation unit 934, and sequentially outputs the video signal to the display device 7. With this configuration, in the display device 7, the normal light image (for example, the normal light image WLI illustrated in FIG. 4), the PDD image (for example, the PDD image SPA illustrated in FIG. 6), and the superimposed image (for example, the superimposed image D1 illustrated in FIG. 7) are simultaneously displayed.

Even in a case where the display mode as described in the second embodiment above is employed, the similar effects as those of the first embodiment are achieved.

Third Embodiment

Next, a third embodiment will be described.

In the following description, the same configurations as those of the first embodiment will be attached with the same symbol, and the detailed description will be omitted or simplified.

In the first embodiment, this disclosure is applied to the medical observation system 1 using the rigid endoscope (the insertion portion 2).

With this regard, in the third embodiment, this disclosure is applied to a medical observation system using a so-called video scope which includes an imaging unit on the distal end of the insertion portion.

Figure 9:
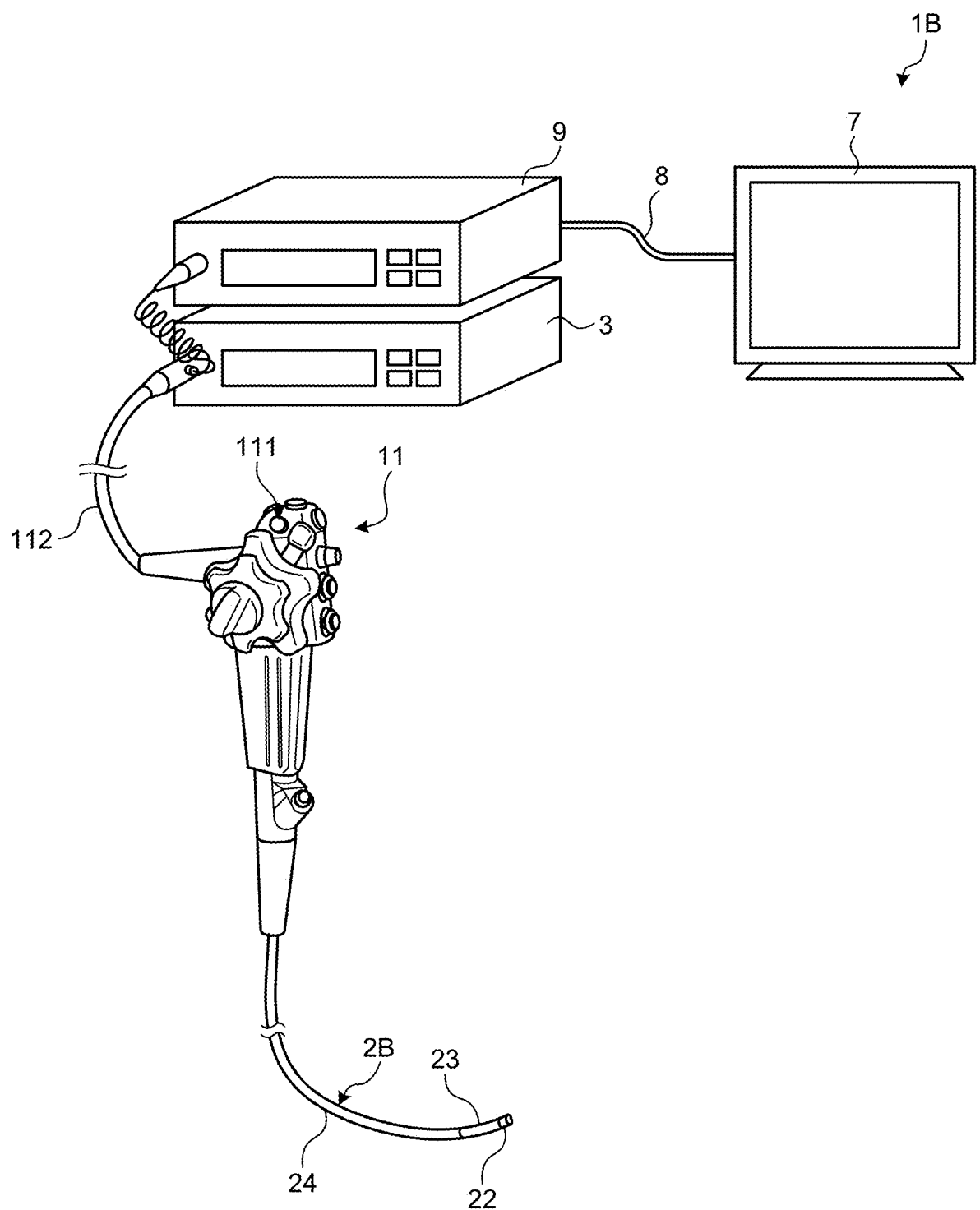
FIG. 9 is a diagram illustrating a configuration of the medical observation system according to a third embodiment.

FIG. 9 is a diagram illustrating a configuration of a medical observation system 1B according to the third embodiment.

The medical observation system 1B according to the third embodiment includes, as illustrated in FIG. 9, an endoscope 11 which captures an in-vivo image of an observation region by inserting an insertion portion 2B to the organism to output the image signal, the light source device 3 which generates illumination light emitted from the distal end of the endoscope 11, the control device 9 which processes the image signal output from the endoscope 11, and the display device 7 which is connected to the control device 9 through the second transfer cable 8 and displays an image based on the video signal processed by the control device 9.

As illustrated in FIG. 9, the endoscope 11 includes the insertion portion 2B which is formed in a flexible elongated shape, an operating unit 111 which is connected to a proximal end side of the insertion portion 2B and receives various operations, and a universal cord 112 which extends in a direction different from the extending direction of the insertion portion 2B from the operating unit 111 and connected to the light source device 3 and the control device 9.

The insertion portion 2B includes, as illustrated in FIG. 9, a distal end portion 22, a bent portion 23 which is flexibly connected to the proximal end of the distal end portion 22, and configured by a plurality of bent pieces, and a long flexible tube 24 which is flexibly connected to the proximal end of the bent portion 23.

Then, the configuration substantially similar to that of the imaging unit 52 described in the first embodiment is embedded in the distal end portion 22 while not illustrated in the drawing in detail. In addition, the configuration substantially similar to that of the communication unit 53 described in the first embodiment is embedded in an operating unit 111 while not illustrated in the drawing in detail. Then, the image signal captured by the distal end portion 22 (imaging unit) is output to the control device 9 through the operating unit 111 and the universal cord 112.

Even in a case where a flexible endoscope (the endoscope 11) is used as described in the third embodiment, the same effects as those in the first embodiment are achieved.

Further, the configuration which performs the display mode described in the second embodiment may be employed in the medical observation system 1B according to the third embodiment.

Fourth Embodiment

Next, a fourth embodiment will be described.

In the following description, the same configurations as those of the first embodiment will be attached with the same symbol, and the detailed description will be omitted or simplified.

In the first embodiment, this disclosure is applied to the medical observation system 1 using the rigid endoscope (the insertion portion 2).

With this regard, in the fourth embodiment, this disclosure is applied to a medical observation system which uses an operating microscope to expand a predetermined view region of a subject inside (organism) and a subject surface (biological surface) to capture an image.

Figure 10:
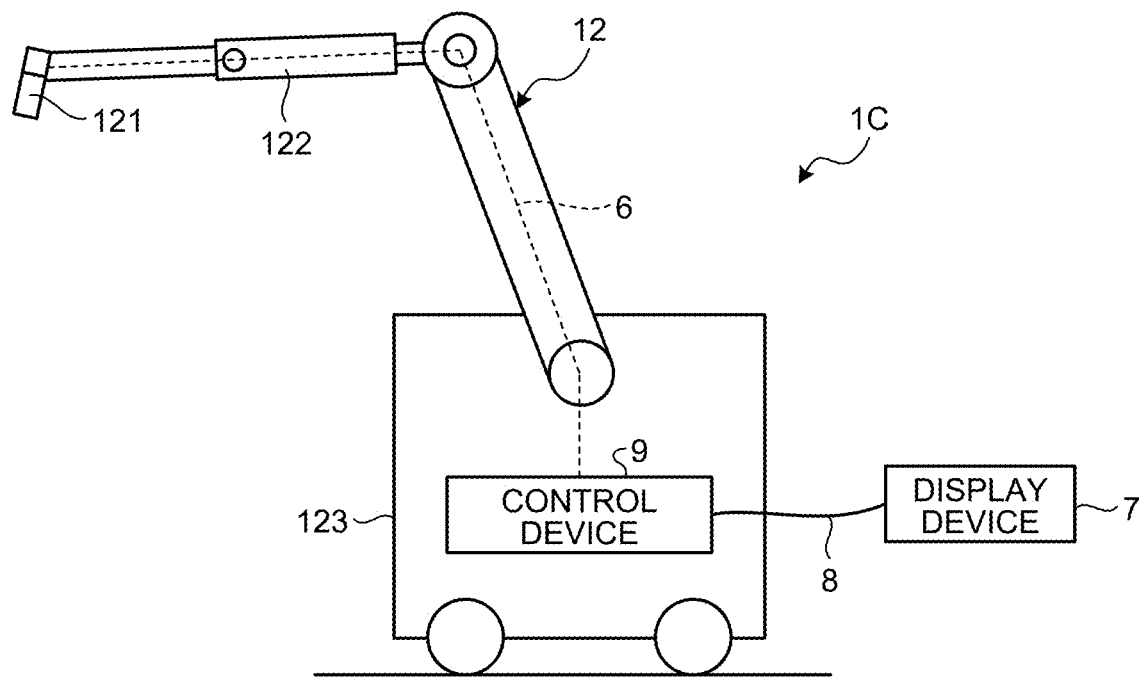
FIG. 10 is a diagram illustrating a configuration of the medical observation system according to a fourth embodiment.

FIG. 10 is a diagram illustrating a configuration of a medical observation system 1C according to the fourth embodiment.

The medical observation system 1C according to the fourth embodiment includes, as illustrated in FIG. 10, an operating microscope 12 which captures an image to observe a subject and output an image signal, the control device 9 which processes the image signal output from the operating microscope 12, and the display device 7 which is connected to the control device 9 through the second transfer cable 8 and displays an image based on the video signal processed by the control device 9.

The operating microscope 12 includes, as illustrated in FIG. 10, a microscope portion 121 which enlarges and captures an image of a minute place of the subject and outputs the image signal, a holding portion 122 which is connected to the proximal end portion of the microscope portion 121 and includes an arm to rotatably support the microscope portion 121, and a base portion 123 which rotatably holds the proximal end portion of the holding portion 122 and is movable on a floor.

Then, the control device 9 is provided in the base portion 123 as illustrated in FIG. 10. In addition, while not specifically illustrated in the drawing, the base portion 123 is provided with the light source device 3 which generates the illumination light to irradiate the subject from the operating microscope 12.

Further, the base portion 123 may be configured to fix and hold the holding portion 122 to the ceiling or a wall instead of being movable on the floor.

The configuration substantially similar to that of the imaging unit 52 and the communication unit 53 described in the first embodiment is embedded in the microscope portion 121 while not illustrated in the drawing in detail. Then, the image signal captured by the microscope portion 121 (imaging unit) is output to the control device 9 through the first transfer cable 6 which is routed along the holding portion 122.

Even in a case where the operating microscope 12 is used as described in the fourth embodiment, the same effects as those of the first embodiment are achieved.

Further, the configuration which performs the display mode described in the second embodiment may be employed in the medical observation system 1C according to the fourth embodiment.

Other Embodiments

Hitherto, the description has been given about embodiments to implement this disclosure, but the disclosure is not limited to the embodiments.

In the first to fourth embodiments, the light source device 3 has been described to emit white light as the normal light of the first wavelength band, and emit the light of a blue wavelength band as the excitation light of the second wavelength band, but the disclosure is not limited thereto. Other light may be employed as the normal light of the first wavelength band and the excitation light of the second wavelength band. In this case, the first and second wavelength bands may be partially overlapped, or may be not overlapped at all.

In the first to fourth embodiments, the first and second periods are set to alternately repeat, but the disclosure is not limited thereto. At least one of the first and second periods continues, and the frequencies of the first and second periods may be configured to have a ratio other than 1:1.

In the second embodiment, the three images of the normal light image, the PDD image, and the superimposed image are simultaneously displayed in the display device 7, but the disclosure is not limited thereto. At least two (for example, two images of the normal light image and the PDD image) of the three images may be configured to be simultaneously displayed. In addition, a plurality of the display devices 7 may be provided to simultaneously display at least two of the three images in different display devices 7.

In the first and second embodiments, part of the configuration of the camera head 5 and part of the configuration of the control device 9 may be provided in the connector CN1 and the connector CN2.

According to the medical control device and the medical observation system of this disclosure, it is possible to generate an image suitable for observation while achieving a simple structure.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical observation system, comprising:
   a light source configured to emit normal light of a first wavelength band and excitation light of a second wavelength band different from the first wavelength band;
   an imaging device including an image sensor; and
   circuitry configured to:
   control the light source to emit alternately the normal light in a first period, and the excitation light in a second period following the first period,
   control the imaging device to cause the image sensor to alternately perform capturing the normal light emitted from the light source and received by way of an observation target in the first period to generate a first captured image, and capturing the excitation light emitted from the light source and received by way of the observation target and fluorescence light from the observation target excited by the excitation light in the second period to generate a second captured image, wherein the normal light includes wavelengths of the fluorescence light,
   perform an adjustment process to reduce a component of a color corresponding to the excitation light included in the second captured image,
   perform a color changing process in which a color of a component of the fluorescence light having a luminance at a pixel position in the second captured image that exceeds a threshold included in the second captured image is changed into a specific color different from the color of the component of the fluorescence light, and
   generate a superimposed image based on the first captured image and the second captured image subjected to the adjustment process,
   wherein the adjustment process is a process in which each light component of colors corresponding to red, green, and blue wavelength bands included in the second captured image is multiplied by specific color correction information to reduce the component other than the component of the fluorescence.

2. The medical observation system according to claim 1, further comprising display controller circuitry configured to generate a video signal to display the superimposed image.

3. The medical observation system according to claim 1, further comprising display controller circuitry configured to generate a video signal to display at least two of the first captured image, the second captured image subjected to the adjustment process, and the superimposed image.

4. The medical observation system according to claim 1, wherein the circuitry is configured to:
   perform first image processing on the first captured image; and
   perform second imaging processing different from the first image processing on the second captured image.

5. The medical observation system according to claim 4, wherein the first image processing and the second image processing include at least one of an optical black subtraction, a white balance adjustment, demosaic processing, color correction matrix processing, a gamma correction, and YC processing.

6. The medical observation system according to claim 1, wherein the circuitry is configured to eliminate a component of the color corresponding to the excitation light included in the second captured image.

7. The medical observation system according to claim 1, wherein the circuitry is configured to perform the adjustment process to reduce a component of the color corresponding to the excitation light included in the second captured image, by reducing both a green (G) pixel value and a blue (B) pixel value of the second captured image.

8. The medical observation system according to claim 7, wherein the circuitry is configured to eliminate both the green (G) pixel value and the blue (B) pixel value of the second captured image.

9. The medical observation system according to claim 1, wherein
   only one image sensor is included in the imaging device.

10. The medical observation system according to claim 1, further comprising a memory, wherein
    the circuitry is configured to transfer a synchronization signal to the light source, the imaging device, and the memory.

11. The medical observation system according to claim 10, wherein
    the light source is controlled by the circuitry to alternately emit the normal light and the excitation light based on the synchronization signal transferred from the circuitry.

12. The medical observation system according to claim 10, wherein
    the circuitry is configured to control, using the synchronization signal, writing of the first captured image to the memory and reading of the first captured image from the memory, and writing of the second captured image to the memory and reading of the second captured image from the memory.

13. The medical observation system according to claim 1, wherein
    the circuitry is configured to repeat the generation of the superimposed image by repeating the control of the light source to emit alternately the normal light and the excitation light, and by repeating the control of the imaging device to cause the imaging device to alternately perform capturing the normal light and capturing the excitation light.

14. The medical observation system according to claim 13, wherein
the circuitry is configured to continuously output a plurality of the repeatedly generated superimposed images.

15. The medical observation system according to claim 1, wherein the adjustment process is a white balance adjustment process in which each of the light components of colors corresponding to the red, green, and blue wavelength bands included in the second captured image is multiplied by a specific gain to reduce the component other than the component of the fluorescence.

16. The medical observation system according to claim 1, wherein the adjustment process is color correction matrix processing in which an input matrix having the light components of colors corresponding to the red, green, and blue wavelength bands included in the second captured image as a matrix element is multiplied by a specific color correction matrix to reduce the component other than the component of the fluorescence.

17. The medical observation system according to claim 1, wherein
the normal light is white light,
the excitation light is light of a blue wavelength band, and
the fluorescence is light of a red wavelength band.

* * * * *